United States Patent [19]
Fugo

[11] Patent Number: 5,411,510
[45] Date of Patent: May 2, 1995

[54] SURGICAL BLADE AND METHOD FOR OCULAR SURGERY

[76] Inventor: Richard J. Fugo, 1507 Plymouth Blvd., Norristown, Pa. 19401

[21] Appl. No.: 85,820

[22] Filed: Jul. 6, 1993

[51] Int. Cl.⁶ .............................................. A61B 17/32
[52] U.S. Cl. .................................. 606/166; 606/167; 30/357; 128/898
[58] Field of Search ............... 606/166, 167, 107, 181; 30/357, 299; 128/898

[56] References Cited

U.S. PATENT DOCUMENTS

| | | | |
|---|---|---|---|
| 1,261,954 | 4/1918 | Newman | 30/299 |
| 5,199,445 | 4/1994 | Rubinfeld | 606/166 |
| 5,234,436 | 8/1993 | Eaton et al. | 606/167 |
| 5,261,923 | 11/1993 | Soares | 606/166 |
| 5,282,816 | 2/1994 | Miller | 606/167 |

FOREIGN PATENT DOCUMENTS 0226787  9/1968  U.S.S.R. ............... 606/167

OTHER PUBLICATIONS

Paul L. Cuzak, M.D., "Cyclodialysis with Goniotomy in Congential Glaucoma," Am. Jour. Ophthalmics, vol. 38, No. 5, Nov. 1954, pp. 712–714.

*Primary Examiner*—Stephen C. Pellegrino
*Assistant Examiner*—William W. Lewis

[57] ABSTRACT

A surgical blade and method incorporating the surgical blade which ensure uniform incision depth and angulation, and the creation of self sealing surgical wounds during cataract surgery.

6 Claims, 3 Drawing Sheets

SURGICAL BLADE AND METHOD FOR OCULAR SURGERY

BACKGROUND-FIELD OF THE INVENTION

This invention relates to ocular surgical instruments and methods, specifically to surgical blades and methods employed in creating incisions during ocular surgery.

BACKGROUND-DESCRIPTION OF PRIOR ART

Opthalmologists currently performing cataract surgery by employing self sealing, no-stitch incisions are faced with the dilemma of creating precise surgical wounds with techniques and instrumentation which defy precision. Ideally, self sealing surgical incisions used in cataract surgery are trifaceted. The first facet is a vertical incision into the outer wall of the sclera, setting the depth for the second facet, the scleral tunnel, which is an incision extending horizontally from the base of the vertical scleral incision into the clear cornea. The third facet is an incision which theoretically extends perpendicularly from the corneal base of the scleral tunnel, downward through the underlying cornea and into the anterior chamber of the eye.

Cataract surgeons refer to the vertical scleral incision as penetrating half of the thickness of the sclera. However, scleral thickness varies from patient to patient and surgeons rely on subjective, imprecise techniques to determine whether the depth of the scleral tunnel is appropriate. Once the vertical scleral incision is made, the depth of which is a product of the surgeon's subjective judgment, a common method for determining appropriate scleral tunnel depth is for the surgeon to attempt to keep the blade used to create the incision in sight through the scleral tissue until the horizontal scleral tunnel incision is completed.

Although the third facet of the self sealing incision is intended to be perpendicular to the corneal base of the horizontal scleral tunnel incision, in practice the angle created is obtuse and the precise measurement of the angle unknown. Currently, the third facet incision is created by extending a straight, sharp surgical blade into the corneal end of the scleral tunnel, then lifting the handle of the blade so that the blade is pointing toward the center of the eye, and plunging the blade through the underlying cornea and into the anterior chamber of the eye. Because the surgical blades presently employed are straight, it is extremely difficult to position a blade in such a manner that it can be plunged through the underlying cornea at an angle perpendicular to the scleral tunnel since the shaft of the blade is resting in a tunnel that is itself intended to be perpendicular to the yet to be created third facet. If two blades are used in the same procedure, the second blade may enter the cornea at a different angle than did the first blade. Moreover, the angles created by this type of incision are non-uniform along the length and width of the incision.

Perpendicularity between the horizontal scleral tunnel incision and the corneal incision is vital to the creation of a true self sealing surgical wound. With a perpendicular corneal incision, the tensile forces within the tissues of the eye push the edges of the incisions together, thereby sealing the surgical wound upon instrument removal. When the angle of the corneal incision is obtuse, the tensile forces within the tissues of the eye may cause the edges of the incison to pull apart or slide over each other, causing complications including an ineffective wound seal, wound gape, hyphema, and induced astigmatism with resultant vision impairment.

These procedures and instrumentation have the following serious complications:

(a) The scleral tunnel depth is set too shallow, in which case the roof of the scleral tunnel may be ripped open during the manipulations required to complete cataract surgery;

(b) When the scleral tunnel depth is set too shallow, the tensile strength of the incised tissues is too weak to form self sealing wounds within the eye;

(c) The scleral tunnel depth is set too deep, in which case the choroidal tissue may be punctured, causing hemorrhaging;

(d) When the scleral tunnel depth is set too deep, the retina may be punctured, in which case the retina may be torn or detached, and intraocular bleeding may occur;

(e) If the scleral tunnel is set too deep, the ciliary body, iris and/or uvea may be penetrated causing bleeding and permanent damage within the eye.

(f) The incision extending from the corneal base of the scleral tunnel, through the cornea and into the anterior chamber of the eye is cut at an angle more than ninety (90) degrees from the corneal base of the scleral tunnel, resulting in an incision which is susceptible to hyphema and wound gape;

(g) The incision extending through the cornea is cut at a non-uniform angle along its width and length, also resulting in an incision susceptible to hyphema and wound gape; and (h) The incision extending through the cornea is not perpendicular to the corneal base of the scleral tunnel resulting in induced astigmatism and increased vision impairment.

OBJECTS AND ADVANTAGES

Accordingly, several objects and advantages of the present invention are:

(a) to provide a surgical blade and method which set a uniform depth for a vertical incision into the sclera;

(b) to provide a surgical blade and method which set a uniform depth for a horizontal scleral tunnel incision, ensuring the incision is not too shallow and preventing tearing of the scleral tunnel incision during cataract surgery manipulations;

(c) to provide a surgical blade and method which set a uniform depth for scleral tunnel incision, ensuring sufficient tensile strength within the incised tissues to effect a self sealing wound;

(d) to provide a surgical blade and method which ensure appropriate scleral tunnel depth, preventing choroidal tissue puncture and consequent hemorrhage;

(e) to provide a surgical blade and method which ensure appropriate scleral tunnel depth, preventing retinal puncture, tearing, and detachment, and intraocular bleeding;

(f) to provide a surgical blade and method which ensure appropriate scleral tunnel depth, preventing penetration of the ciliary body, iris, and/or uvea and consequent permanent tissue damage and intraocular bleeding;

(g) to provide a surgical blade and method that produce an incision perpendicular to the corneal base of a scleral tunnel, which incision extends through the underlying cornea, resulting in a self sealing surgical wound which is not vulnerable to hyphema or wound gape;

(h) to provide a surgical blade and method which produce an incision through the cornea and into the anterior chamber at a uniform angle along the length and width of the incision, resulting in a self sealing surgical wound which is not vulnerable to hyphema or wound gape; and (i) to provide a surgical method and blade that produce an incision perpendicular to the corneal base of the scleral tunnel, which incision extends through the cornea and into the anterior chamber, resulting in a self sealing surgical wound which does not induce astigmatism.

Further objects and advantages of the present invention are to provide improved instruments and techniques for the use of ocular surgeons. Other and further objects and advantages of the present invention will be apparent to those skilled in the art to which it relates or will become apparent from a consideration of the ensuing description and drawings.

DRAWING FIGURES

Figure 1:
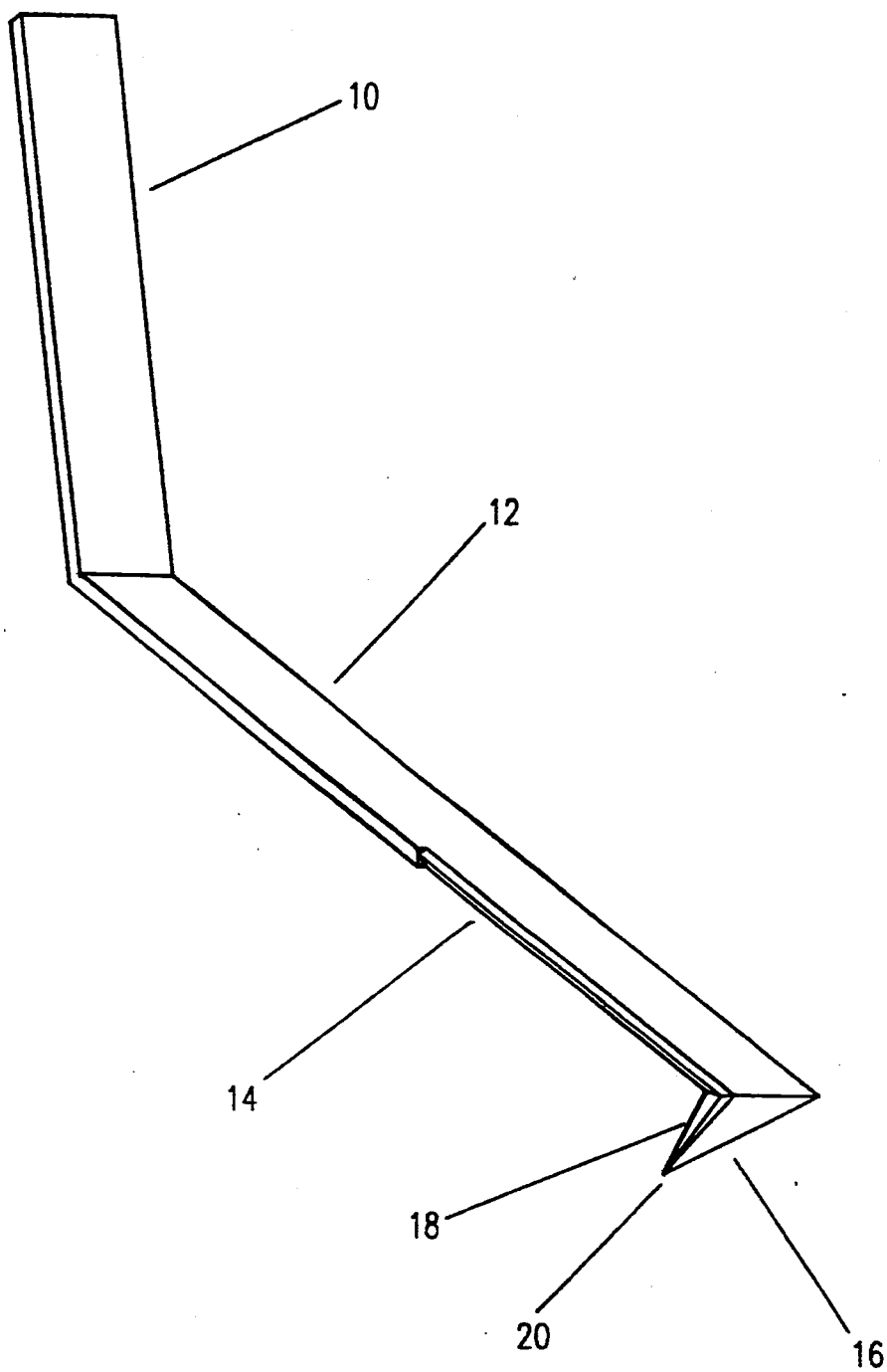
FIG. 1 shows a right-sided view of the surgical blade with an angulated shaft, horizontal stabilizing platform, and angled active tip extending downward from the horizontal stabilizing platform.

| Reference Numerals In Drawings | |
|---|---|
| 10 | Shaft of surgical blade |
| 12 | Horizontal stabilizing platform |
| 14 | Beveled edge of horizontal stabilizing platform |
| 16 | Active tip |
| 18 | Beveled edge of active tip |
| 20 | Active tip point |
| 22 | Vertical scleral incision |
| 24 | Horizontal scleral tunnel |
| 26 | Vertical corneal incision |
| 28 | Surgical blade |
| 30 | Handle |

DESCRIPTION-FIGS. 1 TO 3

Figure 2:
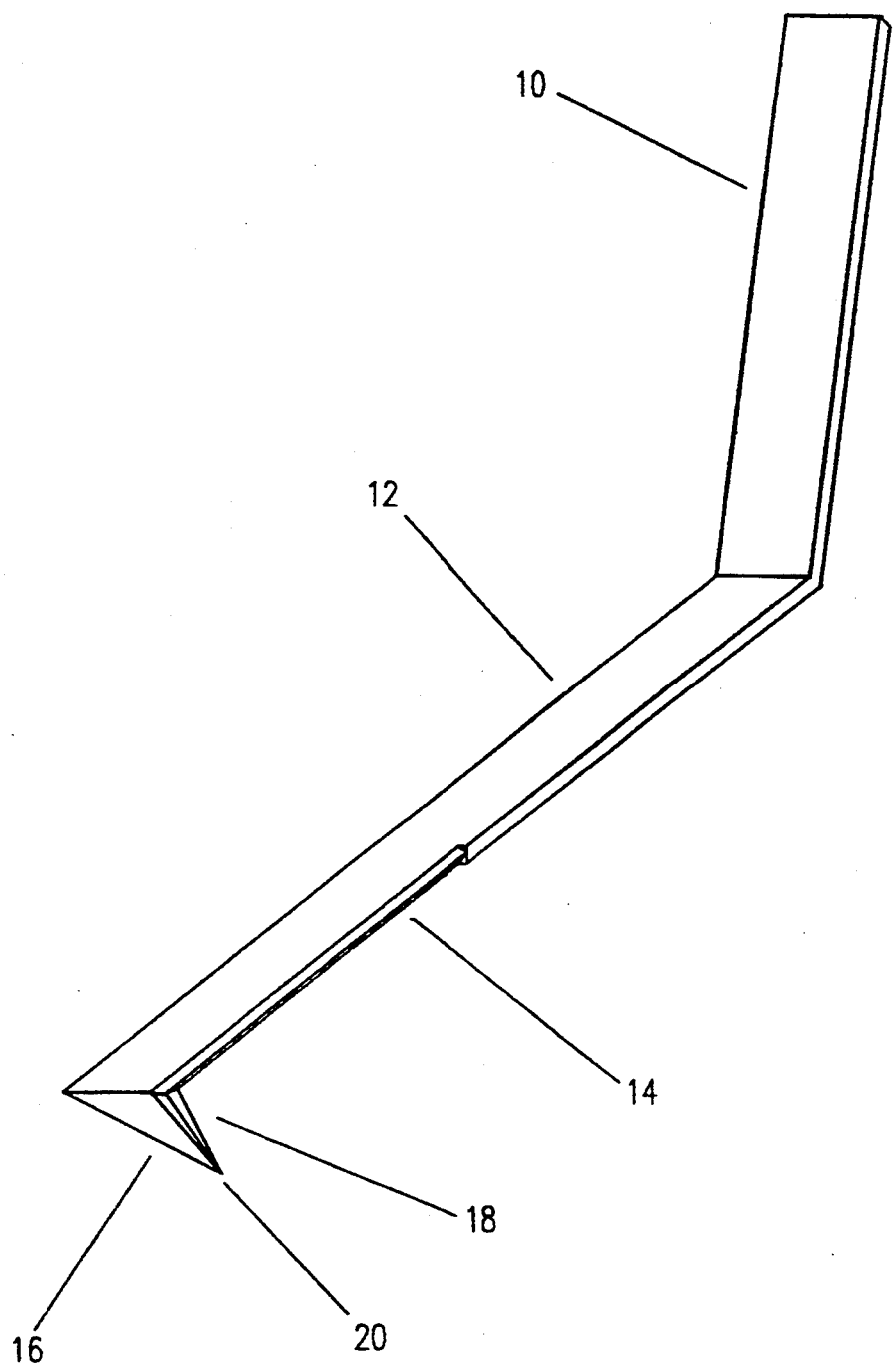
FIG. 2 shows a left-sided view of the surgical blade.

A typical embodiment of the surgical blade of the present invention is illustrated in FIG. 1 and FIG. 2. The surgical blade has an angled shaft 10 for connection to an appropriate handle, a horizontal stabilizing platform 12 with a beveled edge 14 on each side, and a sharp, angled active tip 16 of a known length and angulation, with a beveled edge 18 on each side, extending downward from the horizontal stabilizing platform 12. In the prefered embodiment, the surgical blade 28 is made of metal, the shaft 10 is angled upward from the horizontal stabilizing platform 12 at a forty-five degree angle, the active tip 16 extends downward from the horizontal stabilizing platform 12 at a ninety degree angle in a plane perpendicular to the horizontal stabilizing platform 12, and the active tip point 20 is centrally positioned.

The length of the shaft 10 is typically 7 mm to 25 mm in length and the horizontal stabilizing platform 12 is 3 mm to 10 mm in length and 1 mm to 4 mm in width. The active tip 16 is typically 0.2 mm to 0.6 mm long, although 0.35 mm is the preferred length. Both edges of the horizontal stabilizing platform 12 are sharply center beveled 14 from the angle created by the active tip 16 and extending backward toward the the shaft 10, one-half the length of the horizontal stabilizing platform 12. Both edges of the active tip 16 are completely sharply center beveled 18 and the edges converge to form an extremely sharp, center beveled active tip point 20.

There are various possibilities with regard to the positioning of the active tip 16. The point active tip point 20 formed by the convergence of the edges of the active tip 16 may be situated to the left of center or to the right of center. The edges of the horizontal stabilizing platform 12 and active tip 16 may be beveled in a variety of combinations. The blade edges may all be beveled on the top or on the bottom or the blade edges may be alternatively top and bottom beveled or some of the blade edges may not be beveled. The shaft 10 may be square, cylindrical, or flattened in shape for attachment to an appropriate handle and may extend horizontally from the horizontal stabilizing platform 12 or extend from the horizontal stabilizing platform 12 at a variety of angles. The horizontal stabilizing platform 12 may be rectangular in shape or wider at its shaft end than its active tip end or narrower at its shaft end than its active tip end.

Figure 3:
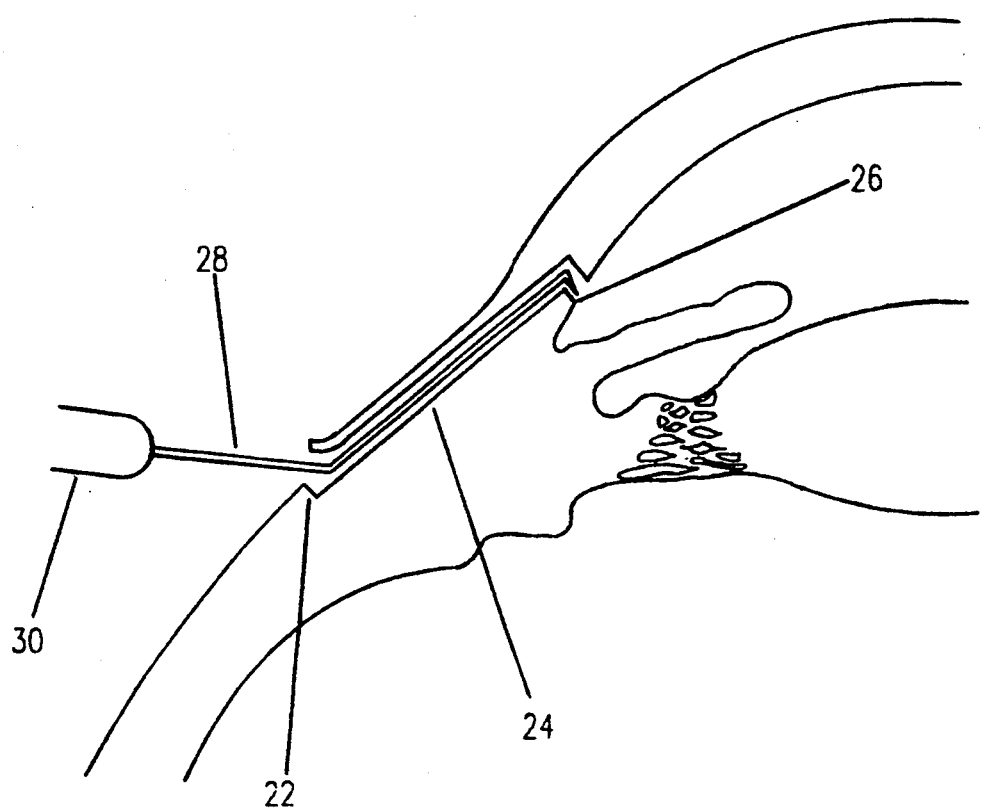
FIG. 3 shows the surgical blade extending into the cornea of the eye, with the active tip penetrating through the underlying portion of the cornea.

FIG. 3 shows a cross sectional view of the eye with a vertical scleral incision 22, horizontal scleral tunnel incision 24, vertical corneal incision 26, which is perpendicular to the horizontal scleral tunnel incision 24 and the intended placement within the eye of the surgical blade 28 which is attached to a handle 30.

OPERATION-FIGS. 1, 2, AND 3

My surgical blade and method provide a safe, efficient solution to the problems created by the failure of instrument technology to keep pace with the advances in ocular surgical techniques. My invention provides an instrument and technique which permits ocular surgeons to make intricate surgical incisions at known depths and angles during cataract surgery, thereby facilitating the creation of true self sealing surgical wounds.

The surgical blade 28 is used to make a trifaceted surgical wound which is self sealing, and does not require suturing to close. The active tip point 20 is used to puncture the sclera and the sclera is pentrated by the active tip 16 to a depth equal to the length of the active tip 16, creating a vertical scleral incision 22 of a known depth. Maintaining contact between the outer scleral wall and the horizontal stabilizing platform 12 prevents penetration into the sclera deeper than the length of the active tip 12.

A typical sclerostomy tunnel blade is then used to create a horizontal scleral tunnel incision 24 of a known depth by extending an incision from the base of the vertical scleral incision 22 and into the clear cornea of the eye in a plane perpendicular to the vertical scleral tunnel incision 22. A sound probe which is 0.3 mm thicker than the active tip 16 is passed through the scleral end of the horizontal scleral tunnel incision 24 and into the clear corneal end portion, thus providing clearance for passage of the surgical blade into the horizontal scleral tunnel incision 24.

The surgical blade 28 is then passed into the horizontal scleral tunnel incision 24 with the active tip 16 reaching to the clear corneal end of the of the horizontal scleral tunnel incision 24. The sound probe is removed and the active tip 16 of the surgical blade 28 is caused to penetrate through the underlying cornea and into the anterior chamber by pushing the handle 30 connected to the surgical blade 28 in an upward and vertical direction, thereby creating a vertical corneal incision 26 which is in a plane perpendicular to the horizontal scleral tunnel incision 24 and passes into the anterior chamber of the eye at a fixed angle as shown in FIG. 3. The vertical corneal incision 26 is then extended to the desired width by moving the surgical blade 28 laterally, creating a uniform incision.

Prior to removal of the surgical blade 28, a sound probe 0.3 mm thicker than the length of the active tip 16 is reintroduced into the horizontal scleral tunnel incision and positioned next to the surgical blade 28. The sound probe handle is gently pushed downward in order to slightly raise the tip of the sound probe probe upward, thereby elevating the roof of the horizontal scleral tunnel incision 24 and creating more space to remove the surgical blade 28.

Upon removal of the surgical blade 28 and the sound probe, the surgical wound created will be sealed due to the tensile forces existing within the eye. The ninety degree internal bevel created between the horizontal scleral tunnel incision and the vertical corneal incision is critical to ensure that the tensile forces of the tissues work to seal the wound, rather than cause the different tissue planes to ride over each other, causing complications including an ineffective seal, wound gape, hyphema, and induced astigmatism with resultant vision impairment.

SUMMARY, RAMIFICATIONS, AND SCOPE

Accordingly, the reader will see that the surgical blade and method of this invention provide a safe, efficient means for ocular surgeons to create self sealing surgical wounds of uniform depths and angulation during cataract surgery. When the surgical blade and method described above are implemented, a perpendicular internal bevel is created between the horizontal scleral tunnel incision and the vertical corneal incision, ensuring a wound that will be sealed by the tensile forces within the tissues of the eye. Further this invention has additional advantages in that it ensures appropriate horizontal scleral tunnel incision depth, thereby preventing tearing of the scleral tunnel during cataract surgery;

it ensures appropriate horizontal scleral tunnel incision depth, thereby maintaining tensile strength within the incised tissues sufficient to form self sealing wounds within the eye during cataract surgery;

it ensures appropriate horizontal scleral tunnel incision depth, thereby preventing puncture and hemmorrhaging of the choroidal tissue;

it ensures appropriate horizontal scleral tunnel incision depth, thereby preventing puncturing and/or tearing of the retina and intraocular bleeding;

it ensures appropriate horizontal scleral tunnel incision depth, thereby preventing penetration of the ciliary body, iris, and/or uvea; and it ensures a vertical corneal incision which is uniform along its width and length.

Although the description above contains many specificities, these should not be construed as limiting the scope of the invention, but as merely providing illustrations of some of the presently preferred embodiments of this invention. For example, the surgical blade may be made of various metals, including stainless steel and titanium; a sound probe or similar device providing the same function may be incorporated into the handle connected to the surgical blade or combined with the surgical blade; the angulation of the shaft of the surgical blade may be varied; the lengths, widths and shapes of the shaft, horizontal stabilizing platform and active tip may be varied; the angulation of the active tip may be varied; the bevels along the blade edges may be varied between top, center, and bottom beveling; the shaft may connected to a variety of handles, including handles made of metal and plastic; and the shaft may be connected to an appropriate handle in a variety of ways, including insertion into a hole centered within the tip of a handle and insertion into a slit cut across the width of the tip of a handle, etc.

Thus, the scope of the invention should be determined by the appended claims and their legal equivalents, rather than by the examples given.

I claim:

1. A method of creating self-sealing surgical incisions in the eye comprising:
   (a) providing a surgical blade of the type which comprises a shaft having a proximal end and a distal end, a horizontal stabilizing platform having a proximal end and a distal end, said proximal end of said horizontal stabilizing platform extending from said distal end of said shaft, and an angled active tip having a predetermined length extending downward from said distal end of said horizontal stabilizing platform at a predetermined angle with respect to said distal end of said horizontal stabilizing platform,
   (b) effecting a vertical incision of a known depth in the sclera of the eye having a proximal end and a distal end by penetrating said sclera with said active tip of said surgical blade to a depth equal to said predetermined length of said active tip,
   (c) effecting a horizontal scleral tunnel incision of a known depth by extending an incision from said distal end of the vertical scleral incision through to the clear cornea of the eye in a plane perpendicular to said vertical scleral incision,
   (d) inserting said surgical blade through the scleral end of said horizontal scleral tunnel incision and into the clear corneal end of said horizontal scleral tunnel incision and, by manipulating a handle connected to said surgical blade, effecting a corneal incision which extends downward from said clear corneal end of said horizontal scleral tunnel incision at a known angle with respect to said clear corneal end of said horizontal scleral tunnel incision; said known angle being defined by said predetermined angle of said active tip of said surgical blade; said corneal incision penetrating through said clear cornea of the eye and into the anterior chamber of the eye, and
   (e) withdrawing said surgical blade from said eye.

2. The method of claim 1 wherein said step of providing comprises providing an active tip which describes an angle of ninety degrees with respect to said distal end of said horizontal stabilizing platform.

3. The method of claim 1 wherein said known angle of said corneal incision with respect to said clear corneal end of said horizontal scleral tunnel incision is ninety degrees.

4. The method of claim 1 further comprising extending said corneal incision to a desired width by manipulating said handle of said surgical blade.

5. The method of claim 1 further comprising inserting a device into said horizontal scleral tunnel incision, whereby said surgical blade can be readily inserted into and withdrawn from the eye.

6. The method of claim 1 further comprising cataract removal.

* * * * *